US00PP36658P2

(12) United States Plant Patent
Kordes

(10) Patent No.: US PP36,658 P2
(45) Date of Patent: May 13, 2025

(54) MINIATURE ROSE PLANT NAMED 'KORpot131'

(50) Latin Name: *Rosa hybrida*
Varietal Denomination: KORpot131

(71) Applicant: W. KORDES' SÖHNE Rosenschulen GmbH & Co KG, Klein Offenseth-Sparrieshoop (DE)

(72) Inventor: Wilhelm-Alexander Kordes, Klein Offenseth-Sparrieshoop (DE)

(73) Assignee: W. KORDES' SÖHNE Rosenschulen GmbH & Co KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 18/989,465

(22) Filed: Dec. 20, 2024

Related U.S. Application Data

(60) Provisional application No. 63/615,082, filed on Dec. 27, 2023.

(51) Int. Cl.
*A01H 5/02* (2018.01)
*A01H 6/74* (2018.01)

(52) U.S. Cl.
USPC ..... Plt./117

(58) Field of Classification Search
USPC ..... Plt./101, 116, 117
See application file for complete search history.

(56) References Cited

U.S. PATENT DOCUMENTS

PP27,185 P3 * 9/2016 Kordes ..... A01H 5/02 Plt./117
PP31,712 P2 5/2020 Kordes

* cited by examiner

*Primary Examiner* — Karen M Redden
(74) *Attorney, Agent, or Firm* — Panitch Schwarze Belisario & Nadel LLP; Stephany G. Small; Travis W. Bliss

(57) ABSTRACT

A new and distinct variety of miniature rose plant, referred to by its cultivar name, 'KORpot131', is described. The new variety forms in abundance on a substantially continuous basis, cream-white colored blossoms. Blooms may continue year-round if grown inside a warm greenhouse. The vegetation is vigorous, and the growth habit is compact. Ornamental foliage is formed.

1 Drawing Sheet

Latin name of genus and species of plant claimed: *Rosa hybrida.*
Variety denomination: 'KORpot131'.

CROSS REFERENCE TO RELATED APPLICATIONS

This application claims priority to U.S. Provisional Application No. 63/615,082, which was filed on Dec. 27, 2023, the contents of which are hereby incorporated herein by reference for all purposes.

STATEMENT REGARDING PRIOR DISCLOSURES BY THE INVENTOR

The first offer for sale of the new variety was February 2023, on the *Rosa danica* website (*Rosa-danica*.dk). The first offer for sale of the new variety was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of miniature rose plant of the present invention was created by controlled breeding in 2018 in Offenseth-Sparrieshoop, Germany by artificial pollination wherein two parents were crossed which previously had been studied in the hope that they would contribute the desired characteristics. The female parent (i.e., the seed parent) of the new variety was an unnamed variety (not patented), which was the product of the cross between an unnamed seedling (not patented) and 'RUlbo807a' (not patented). The male parent (i.e., the pollen parent) of the new variety was the 'KORaroma08' variety (U.S. Plant Pat. No. 31,712).

The parentage of the new variety can be summarized as follows:

(unnamed seedling x 'RUlbo807a') x 'KORaroma08'

The seeds resulting from the above pollination were sown and small plants were obtained which were physically and biologically different from each other. Selective study resulted in the identification of a single plant of the new variety.

The new variety has been found to undergo asexual propagation at Klein Offenseth-Sparrieshoop, Germany by a number of routes such as vegetative cuttings. Asexual propagation techniques in Klein Offenseth-Sparrieshoop, Germany, such as vegetative cuttings, have shown that the characteristics of the new variety are homogeneous, stable, and strictly transmissible by such asexual propagation from one generation to another. Accordingly, the new variety undergoes asexual propagation in a true-to-type manner.

SUMMARY OF THE INVENTION

It was found that the new variety of miniature rose plant of the present invention possesses the following combination of characteristics:

(a) forms cream-white colored blossoms, (b) exhibits a compact growth habit, and (c) provides dark-green colored vegetation.

The new variety well meets the needs of the horticultural industry. It can be grown to advantage as ornamentation in parks, gardens, public areas, and residential landscapes. Accordingly, it is particularly well suited for growing in the landscape.

The new variety can be readily distinguished from its ancestors. More specifically, the seed parent (i.e., the product of (unnamed seedling x 'RUlbo807a')) displays more flower fragrance and a larger flower size compared to the new variety. Additionally, the new variety provides less flower fragrance compared to the flowers of the 'KORaroma08' variety (i.e., the pollen parent). Moreover, the new variety can be readily distinguished from non-parental related similar varieties. For example, the 'KORpot044' variety (U.S. Plant Pat. No. 27,185) displays blossoms with more petals.

The new variety has been named the 'KORpot131' variety.

BRIEF DESCRIPTION OF THE PHOTOGRAPHS

The accompanying photograph shows, as nearly true as it is reasonably possible to make the same in a color illustration of this character, a typical specimen of the new variety and blossoms of the new variety. The illustrated rose plant of the new variety was approximately sixteen weeks of age and was grown indoors on its own roots in a 10.5 cm container in Odense, Denmark in November 2022.

Drawing—illustrates a specimen of the plant displaying flowers at varying points of opening.

DETAILED BOTANICAL DESCRIPTION

The chart used in the identification of colors is that of The Royal Horticultural Society (The R.H.S. Colour Chart, 2015 edition). The terminology which precedes reference to the chart has been added to indicate the corresponding color in more common terms and The R.H.S. Colour Chart designation used herein represents the closest color observed on the majority of the specified botanical feature. The description is based on a one-year-old specimen of the new variety, observed during September, while growing in a one-gallon container on its own roots in a greenhouse in Cochranville, Pennsylvania.

Botanical classification: *Rosa hybrida* cultivar 'KORpot131'.

Commercial classification: Miniature Rose.

Plant:

*Habit*.—Compact.

*Height*.—Approximately 39.0 cm on average from the top of the soil plane when growing in a 1-gallon container.

*Width*.—Approximately 33.0 cm on average.

Branches:

*Stem color*.—Old wood: Green Group 138B. — young stems: Green Group 143A.

*Length*.—Main stems: approximately 39.0 cm on average. — secondary stems: approximately 18.0 cm on average.

*Diameter*.—Main stems: approximately 1.0 cm on average. — secondary stems: approximately 5.0 mm on average.

*Texture*.—Glabrous.

*Prickles*.—Amount: very few. — young prickles: length is approximately 5.0 mm on average; width is approximately 1.0 mm at point of attachment; and color is Greyed-Purple Group 187A. — old prickles: length is approximately 7.0 mm on average; width is approximately 3.0 mm at point of attachment; and color is Greyed-Orange Group 177B.

Leaflets:

*Number*.—3 and 5.

*Shape*.—Ovate; apex is acute and base is rounded.

*Arrangement*.—Odd-pinnate.

*Margin*.—Serrate.

*Undulation*.—None.

*Glossiness of upper side*.—Semi-glossy.

*Texture*.—Upper surface.—Smooth. — under surface: smooth.

*Venation pattern*.—Reticulate.

*Size*.—Terminal leaflet: length is approximately 3.7 cm on average; width is approximately 2.3 cm on average. — lower leaflets: length is approximately 2.6 cm on average; width is approximately 2.0 cm on average. — 5-Leaflet leaf: length is approximately 7.0 cm on average; width is approximately 5.3 cm on average.

Foliage:

*Young foliage*.—Upper surface color: Green Group 143A edged in Greyed-Red Group 182A with venation of Greyed-Red Group 179A. — under surface color: Green Group 143B overlayed with Greyed-Purple Group 185A with indistinguishable venation.

*Old foliage*.—Upper surface color: Green Group 137A with indistinguishable venation. — under surface color: Yellow-Green Group 147B with indistinguishable venation.

*Petiole*.—Texture: upper surface is mostly smooth with sparse prickles; under surface is mostly smooth with sparse prickles. — length: approximately 1.3 cm on average. — width: approximately 1.0 mm on average. — upper surface color: Green Group 143C. — under surface color: Green Group 143C.

*Rachis*.—Length: approximately 1.5 cm on average. — width: approximately 1.0 mm on average. — upper surface color: Green Group 143A. — under surface color: Green Group 143C.

*Stipules*.—Length: approximately 4.0 mm on average. — width: approximately 2.0 mm on average. — margin: entire to erose. — upper surface color: Green Group 143C. — under surface color: Green Group 143C.

Inflorescence:

*Number of flowers*.—About 10 to 15 blooms on average on a plant at once.

*Number of blossoms per stem or in a cluster*.—Typically, 1 bloom per stem on average.

*Peduncle*.—Color: Green Group 143C. — diameter: approximately 5.0 mm on average. — length: approximately 4.0 cm on average. — surface texture: hispidulous.

*Sepals*.—Number: 5. — upper surface color and texture: Green Group 143B, covered in short pubescence. — under surface color and texture: Green Group 143C, puberulent. — size: length is approximately 2.0 cm on average; width is approximately 5.0 mm on average. — margin: entire with occasional extensions on two or three sepals measuring approximately 3.0 mm in length and 1.0 mm in width on average. — shape: lanceolate. — apex: acute to aristate. — base: truncate or flat as it joins the receptacle.

*Buds*.—Shape: ovoid. — size: length is approximately 2.5 cm on average; width is approximately 1.2 cm on average. — color (when opening): White Group 155D.

*Flower*.—Form: double, rosette. — profile: flat. — diameter: approximately 6.0 cm on average. — height: approximately 2.0 cm on average. — duration: on the plant approximately 20 days. — petal color when first and fully opened: upper surface is White Group NN155A with a basal spot of Yellow Group 10B; under surface is White Group NN155A with a basal spot of Yellow Group 10C. — petal color at end of bloom: upper surface is White Group 155C with a hint of Red-Purple Group 65B on the edges with a basal spot of Yellow Group 2B; under surface is White Group 155C with a hint of Red-Purple Group 65B on the edges with a basal spot of Yellow Group 2A. — petals reflex one by one: yes.

*Fragrance*.—Very light sweet fragrance.

*Petal*.—Number: 25 to 30 on average. — drop: average for the type. — length: inner petals are approximately 1.6 cm on average; outer petals are approximately 2.7 cm on average. — width: inner petals are approximately 1.5 mm on average; outer petals are approximately 2.6 cm on average. — overall shape: broadly obovate. — margin: entire with moderate undulation. — apex shape: rounded. — base shape: rounded to cuneate. — texture: upper and lower surfaces are glabrous.

*Petaloids*.—Number: approximately 5 on average per flower. — length: approximately 1.8 cm on average. — width: approximately 7.0 mm on average. — color: upper and under surfaces are White Group 155A with a basal spot of Yellow Group 10B. — texture: smooth. — margin: variable, entire to
erose. — shape: rounded and mostly curving inward. — apex: round. — base: cuneate.

*Stamen*.—Number: approximately 135. — anthers: number is approximately 135; color is Greyed-Orange Group 163A; length is approximately 2.0 mm on average and shape is oval. — filaments: length is approximately 7.0 mm on average and color is Green-Yellow Group 1C.

*Pistils*.—Arrangement: separate and free. — number: approximately 70 on average. — style: length is approximately 5.0 mm on average and color is White Group 155A at the base, transitioning to Greyed-Red Group 179A at the apex. — stigma: diameter is less than 1.0 mm on average; shape is fan shaped; color is Greyed-Red Group 179A.

*Receptacle*.—Diameter: approximately 8.0 mm on average. — depth: approximately 1.0 cm on average. — shape: urn shaped. — color: Yellow-Green Group N144C. — surface texture: smooth.

*Pollen*.—Amount: none observed.

*Hips/seed*.—None observed.

Development:

*Vegetation*.—Dark green and vigorous.

*Blossoming*.—Abundant and continuous; blooms may continue year-round if grown inside a warm greenhouse.

*Resistance to diseases*.—Good resistance to Powdery Mildew (*Sphaerotheca pannosa*) disease under normal greenhouse growing conditions in Cochranville, Pennsylvania.

*Hardiness*.—Unknown.

The new 'KORpot131' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of miniature rose plant named 'KORpot131' characterized by the following combination of characteristics:

(a) forms cream-white colored blossoms, (b) exhibits a compact growth habit, and (c) provides dark-green colored vegetation;

substantially as herein shown and described.

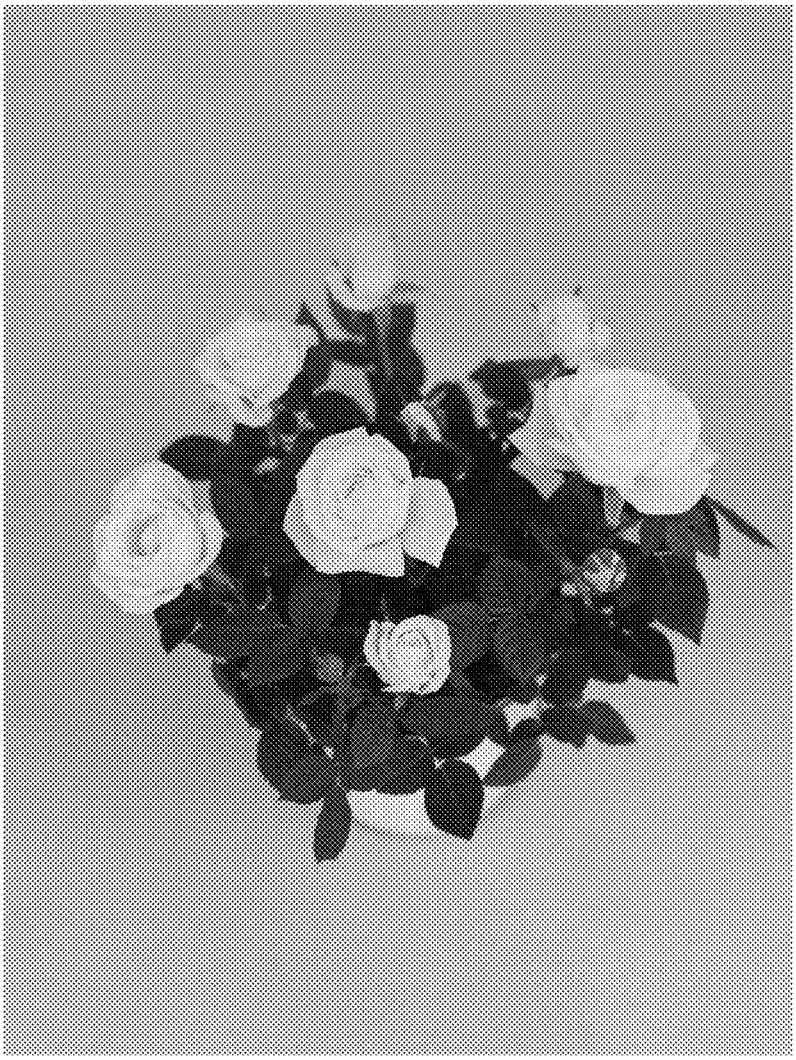

* * * * *